United States Patent
Dunn

(10) Patent No.: US 9,597,484 B2
(45) Date of Patent: Mar. 21, 2017

(54) SURGICAL CAVITY DRAINAGE AND CLOSURE SYSTEM

(75) Inventor: Raymond M. Dunn, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 265 days.

(21) Appl. No.: 14/111,977

(22) PCT Filed: Apr. 13, 2012

(86) PCT No.: PCT/US2012/033608
§ 371 (c)(1),
(2), (4) Date: Oct. 15, 2013

(87) PCT Pub. No.: WO2012/142473
PCT Pub. Date: Oct. 18, 2012

(65) Prior Publication Data
US 2014/0039468 A1 Feb. 6, 2014

Related U.S. Application Data

(60) Provisional application No. 61/475,945, filed on Apr. 15, 2011.

(51) Int. Cl.
*A61M 27/00* (2006.01)
*A61M 1/00* (2006.01)
(Continued)

(52) U.S. Cl.
CPC ....... *A61M 27/00* (2013.01); *A61F 13/00068* (2013.01); *A61M 1/0023* (2013.01);
(Continued)

(58) Field of Classification Search
CPC .............. A61F 13/00068; A61F 13/148; A61F 2013/00174; A61F 2013/00412;
(Continued)

(56) References Cited

U.S. PATENT DOCUMENTS

| 4,257,422 A | 3/1981 | Duncan |
| 4,429,693 A | 2/1984 | Blake et al. |

(Continued)

FOREIGN PATENT DOCUMENTS

| EP | 1320342 A1 | 6/2003 |
| EP | 2094211 A1 | 9/2009 |

(Continued)

OTHER PUBLICATIONS

U.S. Appl. No. 13/675,736, filed Nov. 13, 2012.
(Continued)

*Primary Examiner* — Adam Marcetich
(74) *Attorney, Agent, or Firm* — McCarter & English, LLP

(57) ABSTRACT

A surgical drain device includes an adhesion matrix of biodegradable polymer material and a plurality of drain tubes attached to the matrix. The device is implanted within a surgical wound to treat the presence of seromas, for example, and is used to promote drainage, tissue adhesion, and wound closure. The drain tubes converge into a common collection tube that leads wound fluid outside the body under gravity feed or negative pressure applied to the collection tube. The matrix contains an array of apertures that allow tissue contact across the device. The device also can include a coating of surgical adhesive and a tissue anchoring system of hooks or barbs. The device and systems containing the device are particularly useful to promote the healing of surgical wounds from abdominal surgery.

22 Claims, 8 Drawing Sheets

(51) Int. Cl.
*A61B 17/03* (2006.01)
*A61F 13/02* (2006.01)
*A61F 13/00* (2006.01)
*A61F 13/14* (2006.01)

(52) U.S. Cl.
CPC ........ *A61M 1/0039* (2013.01); *A61M 1/0088* (2013.01); *A61F 13/00072* (2013.01); *A61F 13/0203* (2013.01); *A61F 13/148* (2013.01); *A61F 2013/0054* (2013.01); *A61F 2013/00174* (2013.01); *A61F 2013/00412* (2013.01); *A61F 2013/00536* (2013.01); *A61M 1/008* (2013.01); *A61M 2027/004* (2013.01)

(58) Field of Classification Search
CPC .. A61F 2013/00536; A61F 2013/0054; A61M 1/0039; A61M 1/0088; A61M 27/00; A61B 2017/00004; A61B 17/08; A61B 2017/081; A61B 17/085; A61B 2017/086
See application file for complete search history.

(56) References Cited

U.S. PATENT DOCUMENTS

| | | | |
|---|---|---|---|
| 4,579,555 A | 4/1986 | Russo | |
| 4,608,041 A * | 8/1986 | Nielsen | A61F 13/00068 128/118.1 |
| 4,781,678 A | 11/1988 | de Couet et al. | |
| 5,116,310 A | 5/1992 | Seder et al. | |
| 5,415,715 A | 5/1995 | Delage et al. | |
| 5,549,579 A | 8/1996 | Batdorf et al. | |
| 5,628,735 A * | 5/1997 | Skow | A61F 13/38 604/268 |
| 5,636,643 A | 6/1997 | Argenta et al. | |
| 6,099,513 A | 8/2000 | Spehalski | |
| 6,478,789 B1 | 11/2002 | Spehalski et al. | |
| 6,641,575 B1 | 11/2003 | Lonky | |
| 6,685,681 B2 | 2/2004 | Lockwood et al. | |
| 6,770,794 B2 | 8/2004 | Fleischmann | |
| 6,814,079 B2 | 11/2004 | Heaton et al. | |
| 7,125,402 B1 | 10/2006 | Yarger | |
| 7,182,758 B2 | 2/2007 | McCraw | |
| 7,216,651 B2 | 5/2007 | Argenta et al. | |
| 7,322,971 B2 | 1/2008 | Shehada | |
| 7,351,250 B2 | 4/2008 | Zamierowski | |
| 7,381,211 B2 | 6/2008 | Zamierowski | |
| 7,381,859 B2 | 6/2008 | Hunt et al. | |
| 7,402,620 B2 | 7/2008 | McGhee | |
| 7,410,495 B2 | 8/2008 | Zamierowski | |
| 7,413,570 B2 | 8/2008 | Zamierowski | |
| 7,413,571 B2 | 8/2008 | Zamierowski | |
| 7,438,705 B2 | 10/2008 | Karpowicz et al. | |
| 7,625,362 B2 | 12/2009 | Boehringer et al. | |
| 7,658,749 B2 | 2/2010 | Wittmann | |
| 7,699,831 B2 | 4/2010 | Bengtson et al. | |
| 7,753,894 B2 | 7/2010 | Blott et al. | |
| 7,754,937 B2 | 7/2010 | Boehringer et al. | |
| 7,779,625 B2 | 8/2010 | Joshi et al. | |
| 7,815,616 B2 | 10/2010 | Boehringer et al. | |
| 7,857,806 B2 | 12/2010 | Karpowicz et al. | |
| 7,896,856 B2 | 3/2011 | Petrosenko et al. | |
| 7,981,098 B2 | 7/2011 | Boehringer et al. | |
| 8,030,534 B2 | 10/2011 | Radl et al. | |
| 8,062,331 B2 | 11/2011 | Zamierowski | |
| 8,070,773 B2 | 12/2011 | Zamierowski | |
| 8,079,991 B2 | 12/2011 | Watson | |
| 8,114,126 B2 | 2/2012 | Heaton et al. | |
| 8,123,781 B2 | 2/2012 | Zamierowski | |
| 8,142,419 B2 | 3/2012 | Heaton et al. | |
| 8,172,816 B2 | 5/2012 | Kazala, Jr. et al. | |
| 8,187,237 B2 | 5/2012 | Seegert | |
| 8,188,331 B2 | 5/2012 | Barta et al. | |
| 8,197,467 B2 | 6/2012 | Heaton et al. | |
| 8,273,105 B2 | 9/2012 | Cohen et al. | |
| 8,303,881 B2 | 11/2012 | Lauria | |
| 8,353,931 B2 | 1/2013 | Stopek et al. | |
| 8,399,730 B2 | 3/2013 | Kazala, Jr. et al. | |
| 8,447,375 B2 | 5/2013 | Shuler | |
| 8,777,911 B2 | 7/2014 | Heagle et al. | |
| 2001/0029956 A1 | 10/2001 | Argenta et al. | |
| 2001/0044637 A1 * | 11/2001 | Jacobs | A61B 17/064 606/221 |
| 2002/0077661 A1 * | 6/2002 | Saadat | A61B 17/08 606/221 |
| 2002/0150720 A1 * | 10/2002 | Howard | A61F 13/02 428/131 |
| 2002/0161346 A1 | 10/2002 | Lockwood et al. | |
| 2003/0109855 A1 * | 6/2003 | Solem | A61M 27/00 604/540 |
| 2005/0107756 A1 | 5/2005 | McCraw | |
| 2005/0240220 A1 * | 10/2005 | Zamierowski | A61B 17/064 606/215 |
| 2006/0041247 A1 * | 2/2006 | Petrosenko | A61F 13/00 604/543 |
| 2007/0021760 A1 | 1/2007 | Kelleher | |
| 2007/0021779 A1 * | 1/2007 | Garvin | A61B 17/08 606/216 |
| 2007/0027414 A1 | 2/2007 | Hoffman et al. | |
| 2007/0032763 A1 | 2/2007 | Vogel | |
| 2007/0249999 A1 | 10/2007 | Sklar et al. | |
| 2007/0276316 A1 | 11/2007 | Haffner et al. | |
| 2007/0299541 A1 | 12/2007 | Chernomorsky et al. | |
| 2008/0033324 A1 * | 2/2008 | Cornet | A61B 17/88 601/6 |
| 2008/0033401 A1 | 2/2008 | Watson | |
| 2008/0051832 A1 | 2/2008 | To et al. | |
| 2008/0064953 A1 * | 3/2008 | Falco | A61B 8/483 600/427 |
| 2008/0082130 A1 | 4/2008 | Ward | |
| 2008/0097601 A1 | 4/2008 | Codori-Hurff et al. | |
| 2008/0114297 A1 | 5/2008 | Ambrosio et al. | |
| 2008/0161837 A1 | 7/2008 | Toso et al. | |
| 2008/0167593 A1 | 7/2008 | Fleischmann | |
| 2008/0200950 A1 | 8/2008 | Wohlert | |
| 2008/0300625 A1 | 12/2008 | Zamierowski | |
| 2009/0005744 A1 | 1/2009 | Karpowicz et al. | |
| 2009/0012482 A1 | 1/2009 | Pinto et al. | |
| 2009/0069904 A1 | 3/2009 | Picha | |
| 2009/0105670 A1 | 4/2009 | Bentley et al. | |
| 2009/0137973 A1 | 5/2009 | Karpowicz et al. | |
| 2010/0022990 A1 | 1/2010 | Karpowicz et al. | |
| 2010/0029717 A1 | 2/2010 | Simpson et al. | |
| 2010/0069886 A1 * | 3/2010 | Wilkes | A61M 1/0084 604/543 |
| 2010/0100022 A1 | 4/2010 | Greener et al. | |
| 2010/0160719 A1 | 6/2010 | Kassab et al. | |
| 2010/0160874 A1 | 6/2010 | Robinson et al. | |
| 2010/0179515 A1 | 7/2010 | Swain et al. | |
| 2010/0179516 A1 | 7/2010 | Bengtson et al. | |
| 2010/0234716 A1 | 9/2010 | Engel | |
| 2010/0274177 A1 * | 10/2010 | Rybski | A61M 1/0088 604/20 |
| 2010/0292717 A1 | 11/2010 | Petter-Puchner et al. | |
| 2011/0004168 A1 | 1/2011 | Eriksson et al. | |
| 2011/0028898 A1 | 2/2011 | Clark, III et al. | |
| 2011/0054365 A1 | 3/2011 | Greener | |
| 2011/0071484 A1 | 3/2011 | Song | |
| 2011/0077605 A1 | 3/2011 | Karpowicz et al. | |
| 2011/0130730 A1 * | 6/2011 | Hartwell | A61M 1/0001 604/319 |
| 2011/0282309 A1 | 11/2011 | Adie et al. | |
| 2011/0282310 A1 | 11/2011 | Boehringer et al. | |
| 2011/0301556 A1 | 12/2011 | Lichtenstein | |
| 2012/0025348 A1 | 2/2012 | Marechal et al. | |
| 2012/0041403 A1 | 2/2012 | Bennett et al. | |
| 2012/0059412 A1 | 3/2012 | Fleischmann | |
| 2012/0116334 A1 | 5/2012 | Albert et al. | |
| 2012/0116384 A1 | 5/2012 | Truckai | |
| 2012/0143113 A1 | 6/2012 | Robinson et al. | |
| 2012/0150133 A1 | 6/2012 | Heaton et al. | |
| 2012/0165725 A1 | 6/2012 | Chomas et al. | |
| 2012/0165937 A1 | 6/2012 | Montanari et al. | |

(56) References Cited

U.S. PATENT DOCUMENTS

| | | |
|---|---|---|
| 2012/0172926 A1 | 7/2012 | Hotter |
| 2012/0174380 A1 | 7/2012 | Kennedy et al. |
| 2012/0191054 A1 | 7/2012 | Kazala, Jr. et al. |
| 2012/0197415 A1 | 8/2012 | Montanari et al. |
| 2012/0209226 A1 | 8/2012 | Simmons et al. |
| 2012/0277773 A1 | 11/2012 | Sargeant et al. |
| 2013/0131564 A1 | 5/2013 | Locke et al. |
| 2013/0203012 A1 | 8/2013 | Walker |
| 2013/0274717 A1 | 10/2013 | Dunn |
| 2013/0281784 A1 | 10/2013 | Ray |

FOREIGN PATENT DOCUMENTS

| | | |
|---|---|---|
| EP | 2471462 A1 | 7/2012 |
| EP | 2594299 A2 | 5/2013 |
| WO | WO-2006119256 A2 | 11/2006 |
| WO | WO-2007143179 A2 | 12/2007 |
| WO | WO-2010/097570 A1 | 9/2010 |
| WO | WO-2011091169 A1 | 7/2011 |
| WO | WO-2011/137230 A1 | 11/2011 |
| WO | WO-2012001371 A1 | 1/2012 |
| WO | WO-2012/021553 A1 | 2/2012 |
| WO | WO-2012068052 A2 | 5/2012 |
| WO | WO-2012/082716 A2 | 6/2012 |
| WO | WO-2012/136707 A1 | 10/2012 |
| WO | WO-2013/074829 A1 | 5/2013 |

OTHER PUBLICATIONS

Grabow, Niles, et al., "A Biodegradable Slotted Tube Stent Based on Poly(L-lactide) and Poly(4-hydroxybutyrate) for Rapid Balloon-Expansion", Annals of Biomedical Engineering, vol. 35, No. 12, Dec. 2007, pp. 2031-2038.

Kontakis, George M., et al., "Bioabsorbable Materials in Orthopaedics", Acta Orthopaedica Belgica, vol. 73, Feb. 2007, pp. 159-169.

ProGripTM Mesh: Self-Gripping Mesh for Hernia Repair, McMahon Publishing, Mar. 2012.

International Search Report, PCT/US12/33608, Apr. 13, 2012.

International Preliminary Report on Patentability by the International Bureau of WIPO for international application No. PCT/US13/69916 dated May 19, 2015.

International Search Report and Written Opinion of the International Searching Authority for International Application No. PCT/US13/69916 dated Mar. 27, 2014.

* cited by examiner

SURGICAL CAVITY DRAINAGE AND CLOSURE SYSTEM

CROSS REFERENCE RELATED APPLICATIONS

This application is a 35 U.S.C. §371 national stage filing of International Application No. PCT/US2012/033608, filed Apr. 13, 2012, which claims priority to U.S. Provisional Application No. 61/475,945, filed Apr. 15, 2011. The entire contents of each of the above applications being incorporated herein by reference.

BACKGROUND OF THE INVENTION

A variety of systems have been proposed for draining surgical wounds. The efficacy of such systems has been limited, however, especially for larger surgical spaces or those in which certain characteristics, such as motion or shape, or certain physiological characteristics, such as lymphatic drainage or low protein exist. Seroma is a frequent complication following surgery, and can occur when a large number of capillaries have been severed, allowing plasma to leak from the blood and lymphatic circulation. Surgical wounds that can lead to seroma formation include wounds resulting from surgery involving an abdominal flap, such as abdominoplasty surgery, breast reconstruction surgery, panniculectomy, and ventral hernia repair.

Available surgical drain devices suffer from several deficiencies, particularly when applied following abdominal flap surgery. They fail to drain fluid adequately, are prone to clogging, and fail to promote tissue adhesion within the wound. Thus, there remains a need to develop improved treatments for surgical wounds. The need is particularly acute in abdominal surgery, such as for the prevention and treatment of seromas, but also for any surgical wound predisposed to conditions of excess fluid drainage or tissue motion, or benefiting from tissue adhesion needs, such as pressure ulcers or wounds resulting from a tissue harvesting procedure.

SUMMARY OF THE INVENTION

The invention provides a surgical drain device for the prevention and treatment of seromas as well as for general use in promoting drainage of surgical wounds and wound closure. The drain device includes a plurality of drain tubes disposed on a substrate termed an "adhesion matrix," which is designed to promote tissue adhesion within the seroma or wound space. The adhesion matrix has a conformable configuration and is made of a compliant material having planar surfaces that can curve to adapt to the shape of the wound space.

In a preferred embodiment, the adhesion matrix contains a plurality of apertures, or gaps in the matrix material, which allow tissue contact across the matrix, so as to promote adhesion and wound closure. Thus, a tissue surface on a first side of the matrix can directly contact a tissue surface on a second, or opposite, side of the matrix to promote rapid healing and stabilization of the wound. The number, size and distribution of the apertures extending through the matrix can be selected based on the geometry of the wound. For abdominal wounds, for example, the drain tubes can be positioned in a fan shaped array with a plurality of three or more tubes extending from a manifold. The matrix and/or the tubing can be cut or shaped by the user to conform to the shape of the wound. The matrix can also be used as a medication carrier to assist in the administration of a drug to a patient. The matrix can optionally include a layer of adhesive on at least a portion of any of its surfaces. The drain tubes can be removed from the device once drainage flow is sufficiently reduced, and the adhesion matrix can remain within the body, where it is degraded and absorbed over time, remaining in place to optimize tissue healing. The matrix can comprise a porous biodegradable polymer material. As the plurality of tubes extend from a single exit site into the wound with spaced apart distal ends, a user can readily remove all the tubes simultaneously from the wound.

The surgical drain device can include a tissue anchoring system, whereby the device is mechanically attached to surrounding tissues by an array of surface barbs or hooks. These surface structures can be located on any exposed surface of the adhesion matrix. When the device is implanted, the surrounding tissues can be pressed against the barbs or hooks to embed them within the tissue and anchor the device. The use of surface barbs or hooks can be used in combination with a surgical adhesive, providing a much stronger bond between tissue layers than the adhesive alone, and providing temporary adhesion while the adhesive sets. The structure of the hooks can have various forms depending on the tissue they are intended to bind. Longer hooks can be used for loosely bound tissues such as fat or connective tissue, while shorter hooks can be used for denser tissues such as muscle. Anchors with more rigid stems can be utilized to penetrate denser tissues.

Another aspect of the invention is a system for surgical wound drainage. The system includes the drain device described above together with a vacuum source, such as a pump, and a tube connecting the vacuum source to the drain tubes of the drain device. The system optionally also can include a fluid trap to collect drained fluid and a control unit to monitor and control the application of vacuum and the collection of fluid. Further components of the system can include a vacuum or pressure gauge, a flow meter, and a computer to monitor vacuum and flow and to regulate vacuum or flow.

Another aspect of the invention is a method for treating or preventing a seroma, or promoting the drainage or closure of a surgical wound. The method includes positioning the drain device described above into a seroma, or a surgical wound, such as a wound at risk of forming a seroma, and allowing the device to drain fluid from the wound for a period of time. The device can include surgical adhesive and/or barbs or hooks on its surface to create adhesion between tissue layers within the wound and to anchor the device in place. Drainage can be by gravity flow or can be vacuum assisted by attaching a vacuum source to the drain tubes of the device, using a manifold to merge the flow paths of the drain tubes to a common drain tube for collection. Negative pressure applied to the drain tubes can be used to hold the tissue layers above and below the device together until a surgical adhesive has set, or until the wound healing process binds the tissues together. The application of negative pressure further facilitates contact between tissue on opposite sides of the matrix through the apertures in the matrix to promote tissue adhesion. This improves the rate of healing while at the same time providing for drainage. Optionally, the drain tubes of the device can be removed from the body after drainage flow is reduced, thereby reducing the burden for resorption by the body. Removal of the drain tubes can be facilitated by the inclusion of drain tube channels, or drain tube release tabs, within the adhesion matrix. Release of the drain tubes is then accomplished by sliding the tubes out of the channels or appropriately maneuvering the drain tube assembly to break release tabs. The adhesion matrix is allowed to remain in the seroma or surgical wound where it is resorbed over time.

The flow rate from the drain tubes can be regulated by flow control elements. The flow rate can also be measured or the pressure of fluids can be measured by ultrasound devices or by other methods. The system can also be used in conjunction with wound dressings that can also be attached to a negative pressure source to remove fluids from the wound.

BRIEF DESCRIPTION OF THE DRAWINGS

FIGS. 5A-5D show representative embodiments having different mechanisms of attaching drain tubes to the polymer matrix. In FIG. 5A the drain tubes are encased within drain tube channels, and in FIG. 5B the drain tubes are attached via retaining structures. In FIG. 5C the drain tubes are glued onto the matrix, and in FIG. 5D the drain tubes are spot welded onto the matrix. FIGS. 5E and 5F show embodiments having different configurations of drain tubes within drain tube channels. FIG. 5G shows a drain tube embodiment having lateral apertures for collection of fluid.

DETAILED DESCRIPTION OF THE INVENTION

The present invention provides a surgical drain device, system, and method that allow fluid to be drained from surgical wounds and promote the healing of the wound. Preferred embodiments are used to prevent or treat seromas, for example. The drain device features a set of drain tubes that are attached to a substrate, herein referred to as an adhesion matrix, that is designed to promote adhesion of tissues within the wound or seroma and to encourage cellular infiltration into the device itself. The drain tubes are distributed across the adhesion matrix to promote even drainage across the device. To promote optimum drainage, the drain tubes can be uniformly distributed across the adhesion matrix. The drainage device can be left in place within the wound for a period of time, e.g., until fluid seepage diminishes, after which the drain tubes can be withdrawn from the device and removed from the patient without disturbing the adhesion matrix, which is left in place to biodegrade or become incorporated into the healing process. The device efficiently promotes the healing of even large area wounds such as those resulting from abdominal flap surgery.

Figure 1:
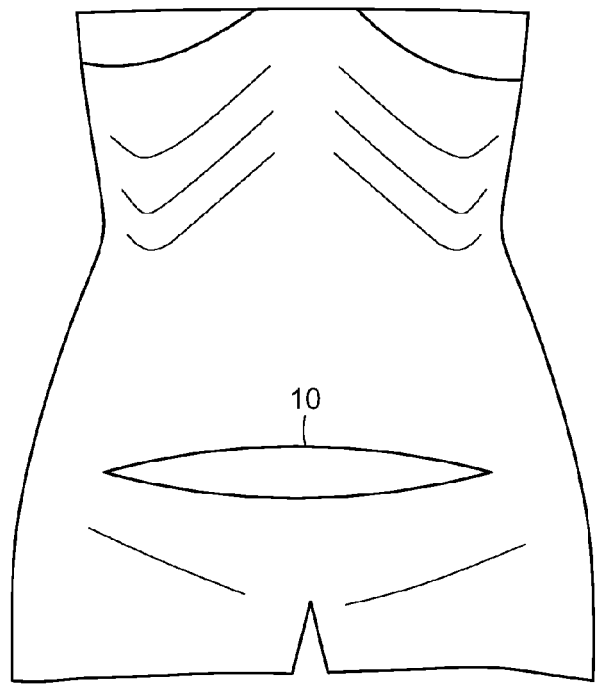
FIG. 1 shows a drawing of the abdomen of a patient who has an abdominal flap wound resulting from abdominal surgery.
Figure 2:
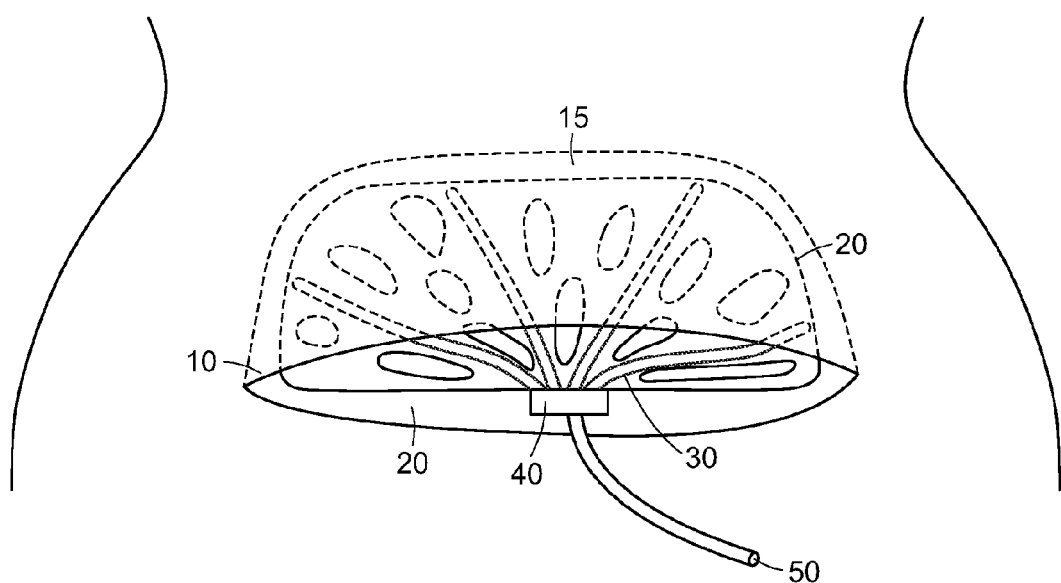
FIG. 2 shows a drawing of a surgical drain device according to the invention which has been inserted through an abdominal flap wound.

A surgical drain device according to the invention is inserted through an incision in the skin of a patient and placed within a wound formed during surgery. A first purpose is to drain fluid during the surgical procedure. The system can be left in place and to provide drainage for days or even weeks following surgery. The device can be used for the treatment of a seroma, e.g., to drain a seroma and thereby promote its healing, it can also be used to prevent seroma formation. For example, the drain device can be placed routinely into surgical incision areas immediately following surgery and used to drain the area and aid in the prevention of seroma formation. Alternatively, the device can be placed into a seroma that has already formed by opening the seroma and installing the device. The use of the drain device is understood to "prevent" seroma formation even if it merely reduces the likelihood of seroma formation. Similarly, the use of the drain device is understood to "treat" seroma formation even if it merely increases the likelihood that the seroma will heal. FIG. 1 shows an abdominoplasty or abdominal flap wound (10) in a patient resulting from abdominal surgery. FIG. 2 shows surgical drain device 20 inserted through abdominal flap wound 10 and into the space occupied by seroma 15.

The device according to the invention includes a number of removable drain tubes 30 attached at their proximal ends to manifold 40, which connects to a vacuum source through vacuum tubing 50. The drain device collects and removes fluid from the abdominal region or from the fluid space of a seroma through the drain tubes, which divert the fluid outside the patient through the aid of a vacuum source. The number of drain tubes can vary depending upon the needs of the device, including the amount of fluid to be drained and the size of the wound and shape of the device. Typically, the device will contain from 2 to about 20 drain tubes. In a preferred embodiment, the device contains preferably at least 3 tubes, and for larger areas such as the abdomen, for example, from about 5 to about 12 tubes.

The drain tubes can be fabricated from any biocompatible thermoplastic or thermoset material. Examples include surgical grade silicone rubber, polyurethane, polyamide, polyimide, PEEK (polyether ether ketone), polycarbonate, PMMA (polymethylmethacrylate), and polyvinylchloride. The drain tubes are intended to be removed after fluid build-up has reduced to a level that is stable without drainage. However, in an alternative embodiment, the drain tubes can be made of a biodegradable material and can be left in place. The drain tubes can be flexible so as to conform to the tissues surrounding the device and to accommodate movement of the patient without causing discomfort. The drain tubes can be open ended or close ended. In a preferred embodiment, the drain tubes are close ended and possess apertures or holes along their length for the uptake of fluid.

Figure 3:
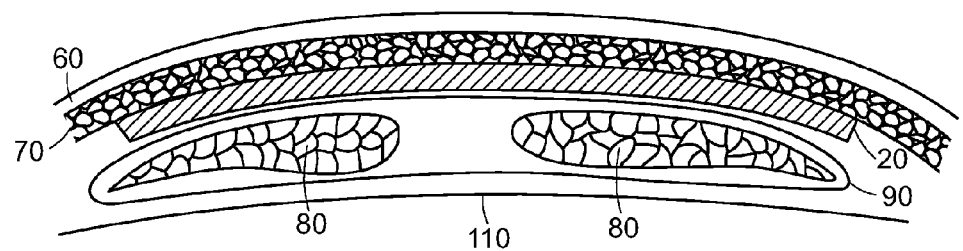
FIG. 3 shows a cross-sectional view of a surgical drain device according to the invention installed in the abdomen of a human patient between subcutaneous tissue and a layer of abdominal muscle.

FIG. 3 shows drain device 20 installed in the abdomen between subcutaneous tissue 70 and a layer of abdominal muscle 80 and associated fascia 90. While this position can be used following abdominal flap surgery, other anatomical locations of the device are also possible and are contemplated as suitable uses of the invention.

Figure 4:
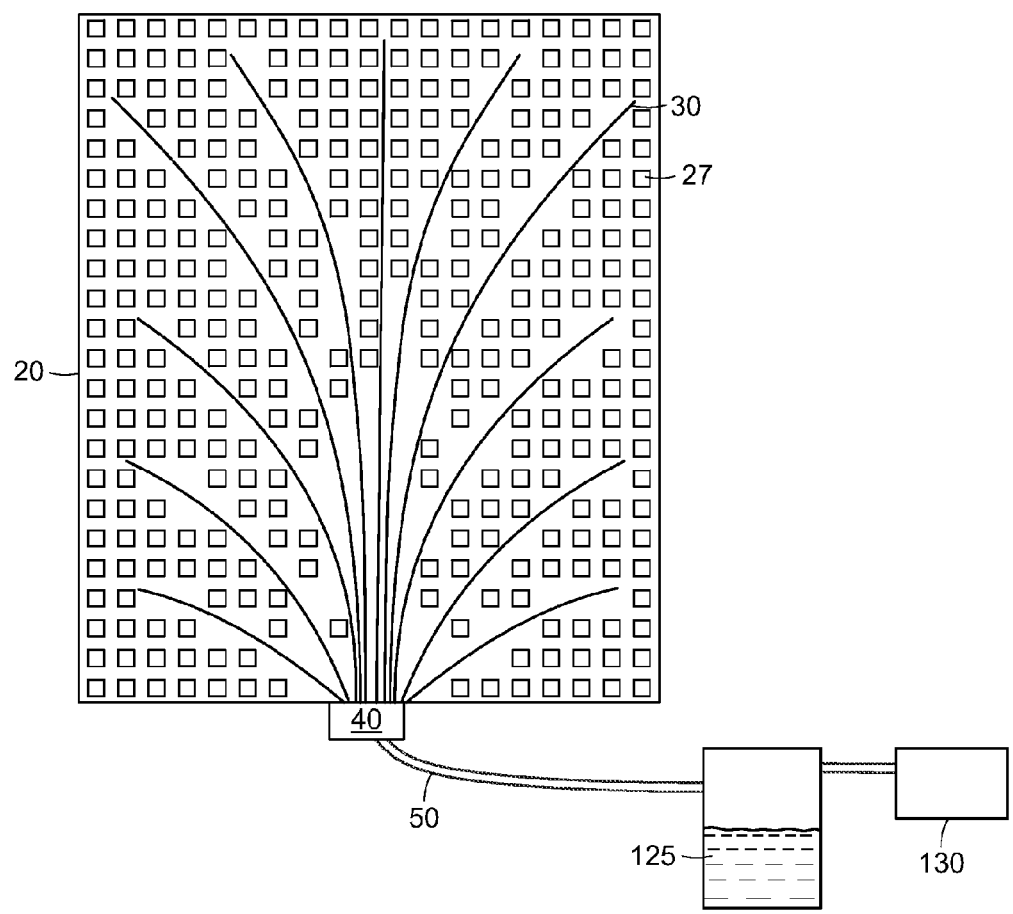
FIG. 4 is a schematic diagram of a surgical wound drainage system according to the invention.

FIG. 4 schematically depicts a system for drainage of a seroma through an abdominal flap wound. System 21 includes drain device 20, having a plurality of drain tubes 30 attached to adhesion matrix 25 and configured so as to drain the full extent of the seroma. The drain tubes are connected at their proximal ends to manifold 40, which is in turn connected through vacuum tubing 50 to a vacuum pump 130 or other vacuum source. Fluid 125 drained from the wound can be optionally accumulated in fluid trap 120. Vacuum pump or other vacuum source 130 can include one or more electronic devices, such as a microprocessor with memory and software, to monitor the vacuum level, pneumatic resistance, and/or fluid removal amount or rate. The electronic device(s) also can be used to control the operation of the system over time according to user-defined parameters, according to a preset program, or in response to data collected on vacuum, resistance, and/or fluid removal.

Figure 5A:
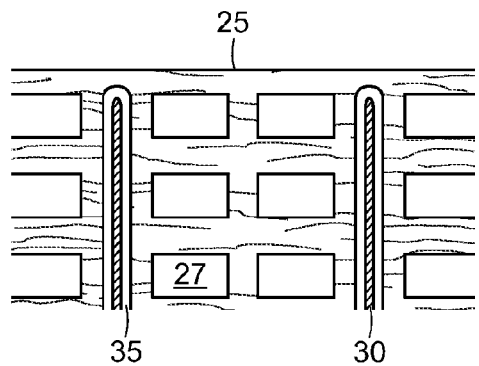
FIGS. 5A-5G are illustrations of embodiments of a surgical drain device according to the invention, depicting the disposition of drain tubes within the device and features of the drain tubes and polymer matrix.

FIGS. 5A-5G depict representative embodiments of a drain device according to the invention, showing several possible configurations of the drain tubes within the device. FIG. 5A shows an embodiment in which each drain tube 30 is disposed within a separate drain tube channel 35. The drain tube channels are embedded within or attached to the surface of adhesion matrix 25 and determine the orientation and distribution of the drain tubes within the device. In a preferred embodiment, the drain tube channels, and consequently the drain tubes, are evenly distributed across the surface area of the drain device, as shown in FIG. 4. These can extend in a generally radial distribution from one edge or region on the matrix to enable use of a single exit tube from the wound. However, the drain tubes can be unevenly distributed if desired, e.g., to increase the drainage capacity or rate from specific areas of the device. The use of drain tube channels ensures that the drain tubes remain in position within the patient and ensures that the drain tubes can be removed easily at the appropriate time, without disrupting the wound healing process. Drain tube channels require a mechanism to accept fluid and pass it on to the drain tubes within. Suitable mechanisms include using apertures or holes of any desired shape and distribution along the length of the channels (see, e.g., apertures 33 on channels 35 in FIG. 6D), and using a porous material to form the drain tube channels (see drain tube channels 35 in FIGS. 5E and 5F, constructed of a porous polymer matrix).

Figure 5B:
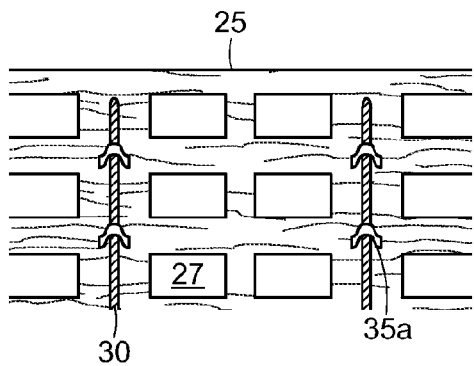
Figure 5C:
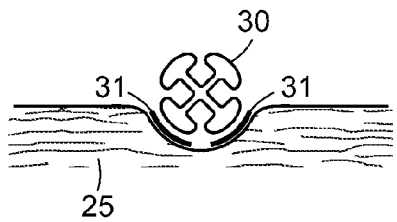
Figure 5D:
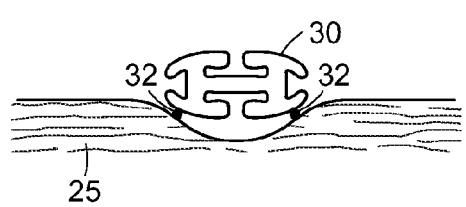

Several alternative embodiments are also contemplated which lack drain tube channels. FIG. 5B depicts the use of retaining structures 35a instead of channels in order to removably attach the drain tubes to the adhesion matrix, while allowing removal of the tubes by sliding or by breaking off the retaining structures. The retaining structures can have any form compatible with their function. FIG. 5C shows an embodiment in which drain tube 20 is held in place by layer of adhesive 31, and the tube is fitted within a depression on the surface of adhesion matrix 25. In the related embodiment shown in FIG. 5D, the drain tube is held in the matrix depression by spot welds or adhesion points 32, which can be broken through suitable manipulation to remove the tubes.

Figure 5E:
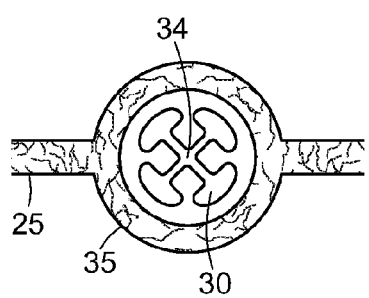
Figure 5F:
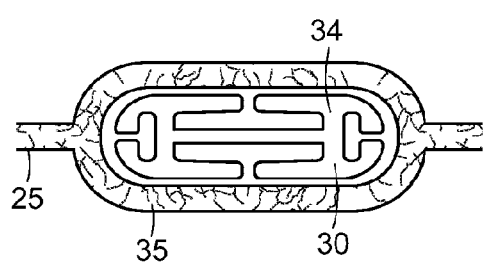

FIGS. 5E and 5F present cross-sectional views of a portion of the adhesion matrix 25 of an embodiment of a drain device according to the invention. The adhesion matrix contains regions for receiving drain tubes or can include one or more drain tube channels 35 which surrounds drain tubes 30, having lumen 34, through which seroma or other wound fluid is removed. A round Blake drain is depicted as the drain tube in FIG. 5E, and a flattened version in FIG. 5F. A variety of drain tube profile shapes are possible, including oval, elliptical, square, rectangular, triangular, flattened, compound (i.e., having 2 or more parallel lumens, interconnected or separated), or irregular. The drain tubes optionally can be coated with a lubricant on their outer surfaces to facilitate their removal from the channels.

Figure 5G:
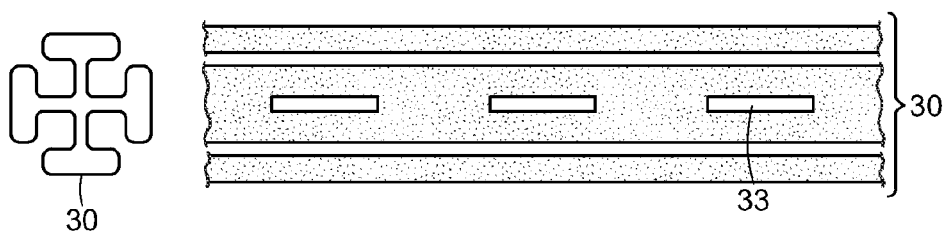

In a preferred embodiment the drain tubes possess openings or apertures 33 along their length to permit fluid to enter for drainage. FIG. 5G depicts one such embodiment. The relative surface area and distribution of such apertures can be chosen so as to regulate flow through the drain tubes. For example, pressure drop (i.e., loss of vacuum) along the length of the drain tubes can be compensated by increasing the open surface area or the density of apertures towards the distal end of the drain tubes. Drain tubes are preferred which have an aperture distribution that provides an essentially constant rate of fluid uptake along the length of the drain tubes (e.g., increasing aperture area towards the distal end), so that uniform drainage is obtained across the drain device.

Adhesion matrix 25 includes a plurality or matrix of apertures 27 which allow tissue contact through the drain device. Such tissue contact promotes wound healing and the sealing of capillaries, which is important for treating seromas or preventing their formation. In the drain device according to the present invention, the promotion of tissue contact works in combination with fluid drainage to promote wound healing. The adhesion matrix 25 and its drain tube channels 35 preferably are constructed of one or more biodegradable polymer materials and can be left within the wound, where they stabilize tissue infiltration and adhesion and thus promote the healing process. The size, shape, and distribution of the tissue contact apertures 27 can be varied according to individual needs. However, greater tissue contact across the device will promote better adhesion, drainage, and wound closure. Therefore, it is preferred that at least about 50%, 60%, or 70%, and preferably about 75-80% of the total surface area (one side) of the drain device remains open in the form of tissue contact apertures. The distribution and spacing of tissue contact apertures can be varied as desired, and the apertures can be the same, similar, or different in shape, size, and distribution across the device. For example, the apertures can be distributed with an average center-to-center spacing in the range of about 2 mm to about 20 mm or more, and the average individual aperture surface area can be in the range from about 1 mm$^2$ to about 5 cm$^2$. In a preferred embodiment, the apertures have about 1 cm$^2$ average surface area, and their number or their collective surface area become progressively larger from the proximal end of the drain device (i.e., near the exit point from the body) toward the distal end of the device (deep within the wound or seroma), so that tissue adhesion and wound closure progress from deep within the wound towards the surface of the body.

Figure 6A:
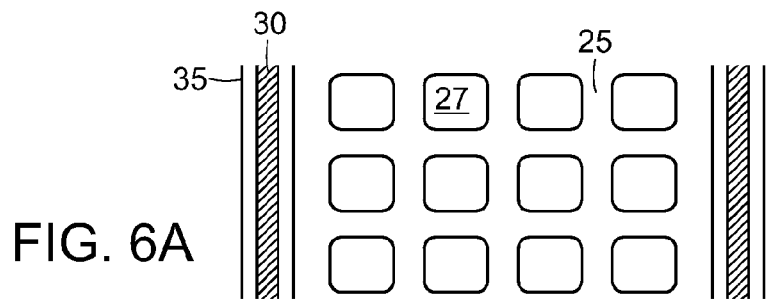
FIGS. 6A-C show illustrations of embodiments of an adhesion matrix having different types of tissue contact apertures.
Figure 6B:
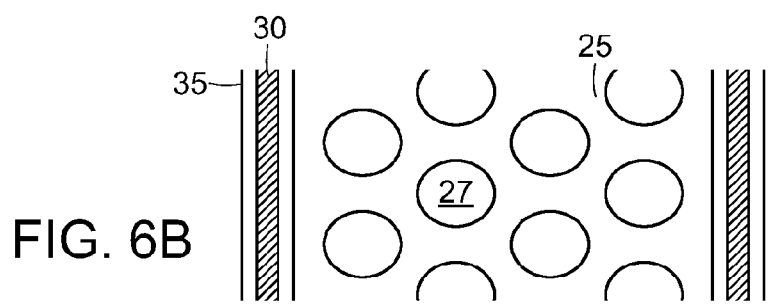
Figure 6C:
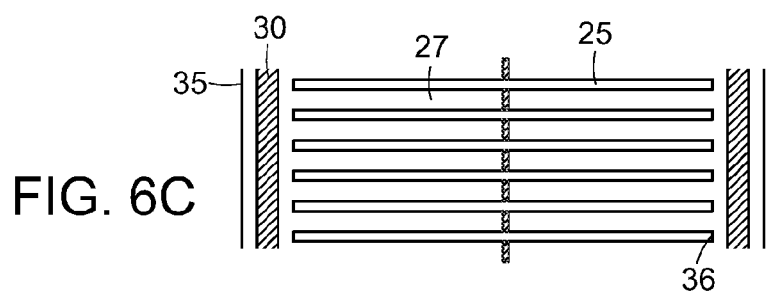
Figure 6D:
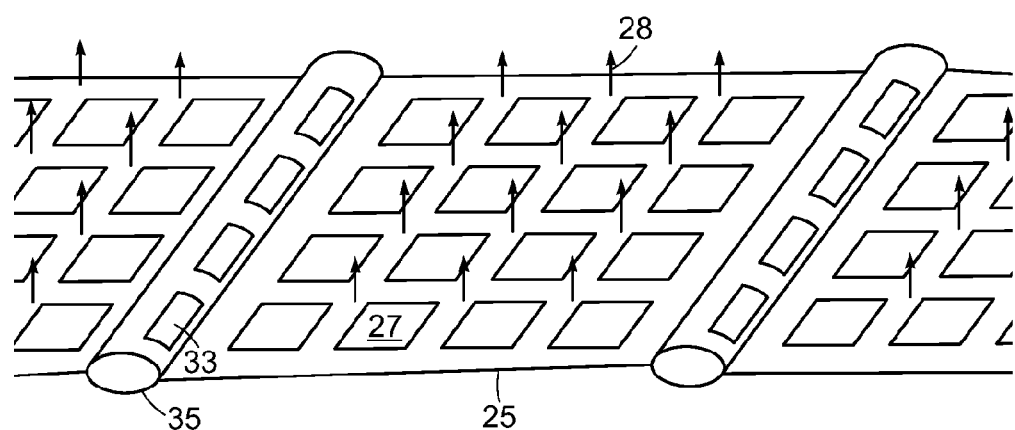
FIG. 6D is an illustration of an adhesion matrix embodiment possessing tissue anchors on its surface.
Figure 6E:
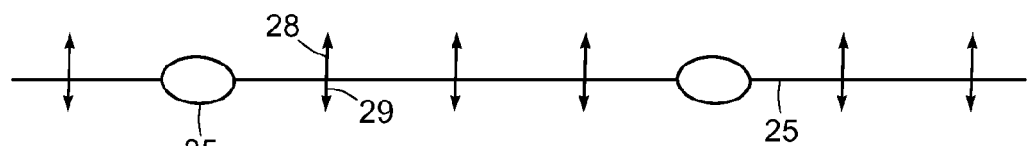
FIG. 6E shows a cross-sectional view of the adhesion matrix of FIG. 6D.

FIGS. 6A-E show several embodiments of the adhesion matrix. A portion of the adhesion matrix 25 between two neighboring drain tubes 30 and drain channels 35 is shown. The embodiment shown in FIG. 6A has a regular arrangement of rectangular apertures 27 to allow tissue contact through the device. Circular apertures are shown in FIG. 6B. The embodiment of FIG. 6C includes apertures 27 that are formed into lateral channels. Fluid flows laterally through these channels toward openings 36 in the drain tube channels, drawn by the reduced pressure in the drain tubes. As shown in FIGS. 6D and 6E, the surfaces of the adhesion matrix, including the drain channels, can be endowed with an array of hooks or barbs to promote anchoring of the device to adjacent tissues. In the embodiment shown in FIG. 6E, the hooks on the upper side 28 are longer than the hooks on the lower side 29. This arrangement can be used where the tissues on either side of the device are of different density. For example, longer hooks such as about 1.5 to about 3 mm in length are preferred for less dense tissue, such as subcutaneous fat tissue, whereas shorter hooks such as about 0.5 to about 1.5 mm in length are preferred for denser tissues such as fascia and muscle.

The adhesion matrix, including any drain tube channels and hooks or barbs, can be fabricated from a biodegradable polymer material, as these structures are intended to remain in place in the patient's body after removal of the drain tubes, so as not to disrupt the healing process. Examples of suitable biodegradable or resorbable materials include Vicryl (polyglycolic acid), Monocryl (glycolic acid-ε-caprolactone copolymer), PDS (polydioxanone, PDO), PLA (polylactic acid, polylactide), PLLA (poly-L-lactic acid), PDLA (poly-D-lactic acid), PGA (polyglycolic acid, polyglycolide), PLGA (poly(lactic-co-glycolic acid)), PHB (polyhydroxybutyrate), and PCL (polycaprolactone). In a preferred embodiment, the adhesion matrix, including any drain tube channels, is formed of an open network of polymer chains that has sufficient porosity to allow infiltration by cells and fluid flow across the material. Cellular infiltration can promote tissue adhesion and the biodegradation of the polymer after the wound has healed. In some embodiments, the adhesion matrix including any drain tube channels is permeable to seroma fluid but not permeable to cells. In other embodiments, the adhesion matrix, including any drain tube channels, is permeable to fluid and electrolytes but is impermeable to proteins. The permeability properties of the matrix polymer material that makes up the basic substrate of the matrix can be the same or different compared to the material that makes up the drain tube channels. In a preferred embodiment, the polymer chains, or fibers composed of polymer chains, of the adhesion matrix are aligned along an axis substantially perpendicular to the axes of the nearest drain tubes. This alignment pattern promotes the flow of fluid through or along the surface of the adhesion matrix towards the drain tubes.

The adhesion matrix, and thus the overall drain device, can have any form suitable for insertion into the wound or seroma where it is to be inserted. Generally, the form is that of a thin sheet having an essentially rectangular shape. However, the shape can be rounded, circular, elliptical, oval, or irregular. Preferably the corners are rounded so as to minimize mechanical irritation of surrounding tissues. The size of the device is also determined by the particular use and anatomy of the patient. For example, the adhesion matrix can have an overall width and length in the range from about 2 cm to 25 cm, such as about 10 cm×12 cm or about 20 cm×25 cm. The thickness of the adhesion matrix can be from about 0.5 mm to about 1 cm; where the sheet of material is preferably less than 5 mm in thickness and preferably the adhesion matrix is about 1-2 mm thick. The thickness of the entire drain device, including the sheet of the adhesion matrix, drain tubes, and any hooks or glue pads is about 5 mm or less, 10 mm or less, or about 5-10 mm.

Figure 7A:
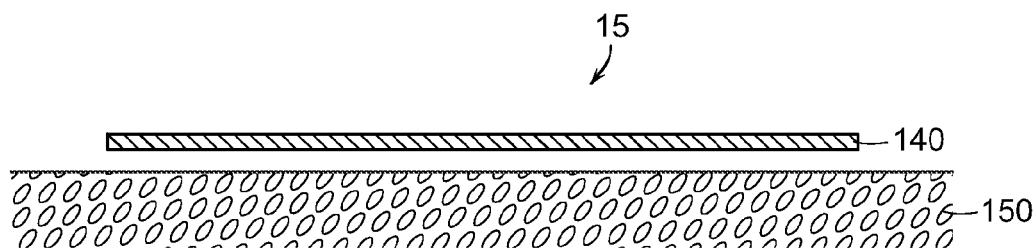
FIGS. 7A-7C are cross-sectional illustrations of different embodiments of the drain device positioned within a wound or seroma. These embodiments include one or more layers of adhesive.
Figure 7B:
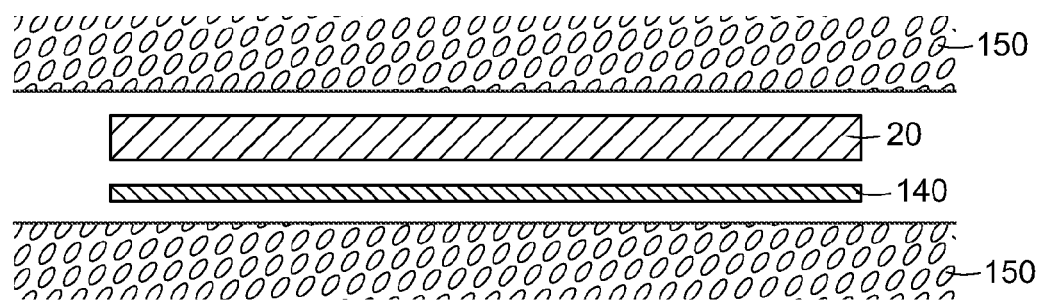
Figure 7C:
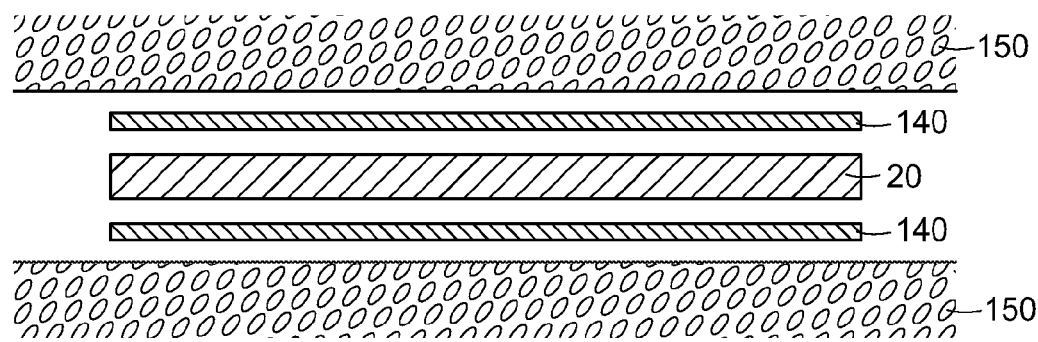

The adhesion matrix can be coated with an adhesive material such as a surgical glue either in addition to or instead of using hook or barb structures that stabilize tissue layers on either side of the drain device. Any type of surgical adhesive suitable for use within the body can be used, including polyethylene glycol polymers, adhesive proteins, gelatin-thrombin mixtures, albumin-glutaraldehyde, and fibrin-based sealants. Cyanoacrylates are to be avoided, as they cause inflammation if used internally. An adhesive coating can be placed on one or both surfaces of the adhesion matrix. Adhesive coatings can be applied to the device prior to its placement in a patient, i.e., as part of the device fabrication process. An adhesive coating can cover all or a portion of a surface of the device. A surgical adhesive can be used in the form of a fibrous mat or pad that is soaked with an adhesive composition. The mat or pad is preferably fabricated from a biodegradable polymer, such as the type used to prepare the adhesion matrix. One or more layers of adhesive material can be placed between the device and surrounding tissue at the time of placement in the patient. FIGS. 7A-7C illustrate the placement of supplemental adhesive layers with the drainage device. In FIG. 7A, adhesive layer or pad 140 has been placed into a wound or seroma adjacent to exposed tissue 150. In FIG. 7B, drainage device 20 has been placed onto the adhesive layer as shown in FIG. 7A, and the wound then closed and vacuum applied, so that the device-adhesive pad sandwich is surrounded by tissue 150. FIG. 7C depicts the structure obtained if a second adhesive pad or layer 140 is added adjacent to the drainage device on the opposite side of the first adhesive layer.

Figure 8:
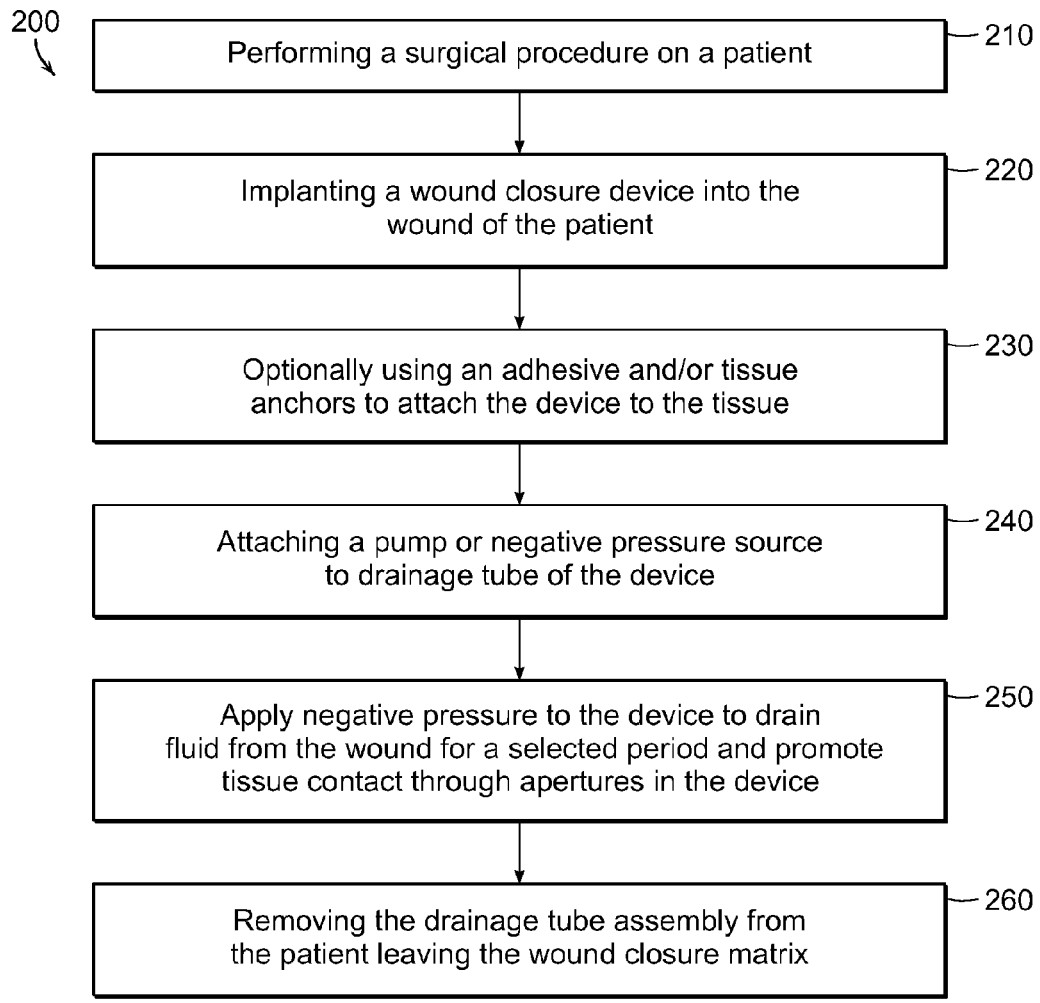
FIG. 8 illustrates a process sequence of performing wound closure treatment in accordance with preferred embodiments of the invention.

The invention also provides a method for treating or preventing a seroma as illustrated in FIG. 8. The method also can be used to promote wound closure after surgery 210, to prevent infection after surgery, and to improve the strength and/or cosmetic appearance of a surgical wound after it has fully healed. A drain device according to the invention is positioned into a surgical wound 220, such as a wound following abdominal flap surgery. The device has been sterilized prior to placement within the wound. Optionally, one or more layers of surgical adhesive is placed on one or both sides of the device, interfacing between the device and surrounding tissue 230. If the device includes hooks or barbs on one or both sides, pressure is applied to the surface of the device in order to set the hooks or barbs into the surrounding tissue. The wound is then partially surgically closed at the surface, leaving a single tube exiting the wound. The tube is then attached to a vacuum source 240, and vacuum is applied 250 so as to initiate drainage through the device. The rate of drainage is controlled by the level of vacuum applied. The amount of vacuum is sufficient to promote drainage without causing damage to the tissues surrounding the implanted device. For example, the vacuum can be in the range from about 75 to 250 mm Hg. After the rate of fluid drainage has decreased to acceptable levels, the vacuum is removed and the drain tubes are removed 260 by slowly pulling them out through the remaining wound opening, which is subsequently closed. The adhesion matrix remains in the patient and is biodegraded and absorbed over a period of weeks to months.

Figure 9A:
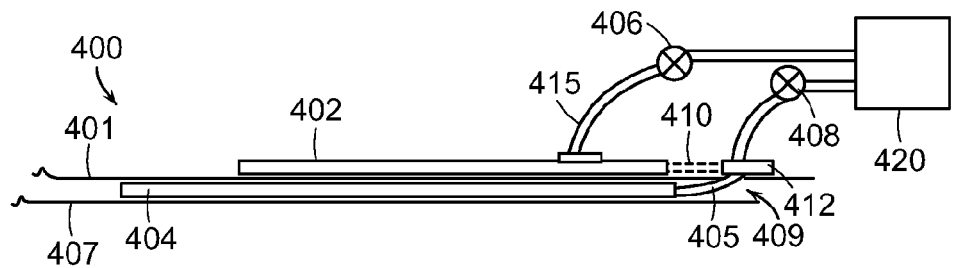
FIG. 9 illustrates a wound drainage and wound dressing system in which the wound dressing does not overlie the drainage exit site.
FIG. 9B illustrates a wound drainage and dressing system in which the wound dressing overlies the drainage exit site.
Figure 9B:
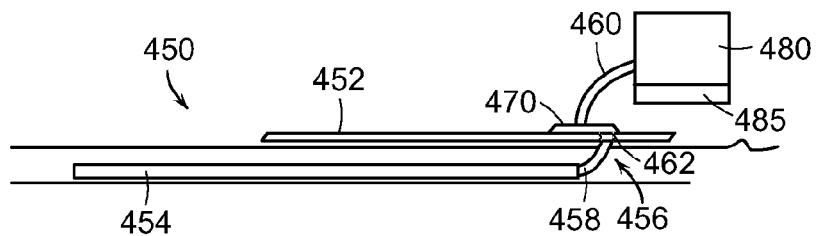

Illustrated in connection with FIGS. 9A and 9B are uses of a wound dressing in combination with the adhesion matrix or mesh device and a negative pressure drainage system. After placement of the matrix 404, as described in detail herein, the drainage tubing 405 extends through an exit site 409 of the skin 401 of a patient. The wound can frequently require the use of a wound dressing 402 that is placed externally on the skin of a patient. The wound dressing can either overlie the exit site 456 as shown in FIG. 9B, or the wound dressing can be placed laterally (or non-overlying) from the exit site 409 as shown in FIG. 9A. The tubing 405 can either connect directly to the pump 420, or can utilize a connector or manifold 412 positioned on or above the skin 401, which can be connected to the pump 420. A valve 408 can be used to control the application of negative pressure. A flow meter can be included at the connector or manifold 412 or at the valve 408 to measure the fluid removal rate and total amount of fluid removed. A quantitative measure of the fluid removed can thereby be measured and recorded. Other diagnostic measurement devices, such as ultrasound, can also be used to measure the amount and location of fluid or seromas within the wound. This information can be used to adjust the amount and distribution of negative pressure applied within both the wound using drainage system 404, 454 and the wound dressing 402, 452.

Negative pressure can be applied to the wound dressing 402 through separate tube 415 that can be attached to the same pump 420 as the drainage system or a second pump. A valve 406 can be used to regulate pressure to the wound dressing. In the embodiment of FIG. 9B, tube or tubes 458 can exit the wound and attach at connector 462 to the underside of the dressing 452. A manifold 470 can control the distribution of negative pressure to both the dressing 452 and the drainage device 454 using passive or active flow control elements. The manifold can be attached using a single tube 460 to pump 480. The pump 420, 480 can be operated by hand or electronically. The pump can have internal electronic control, memory and display features 485 to control system operation and record patient data.

Figure 10A:
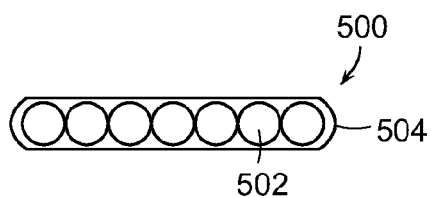
FIGS. 10A and 10B illustrate cross-sectional view of drainage exit tube assemblies that can be used in preferred embodiments of the invention.
Figure 10B:
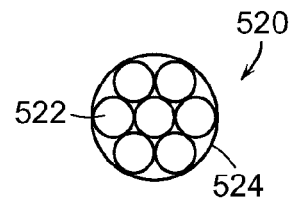

Shown in FIGS. 10A and 10B are preferred embodiments of drainage tube assemblies that can be used in conjunction with the invention. The drainage tubing 405, 458 preferably exits the wound as a single tube or as a cluster of tubes within an outer tube. The outer tube 504 can either be a flattened shape 500 of a plurality of three or more tubes 502 arranged in line as shown in FIG. 10A, or can be circular 520 with drainage tubes 522 extending within outer tubes 522 to the pump or connector. In certain applications, it may be advantageous to remove the tubes separately at different times from the drainage system as certain regions may drain more quickly. However, for many wounds it is useful to simultaneously remove all drainage tubes from the wound.

Figure 11:
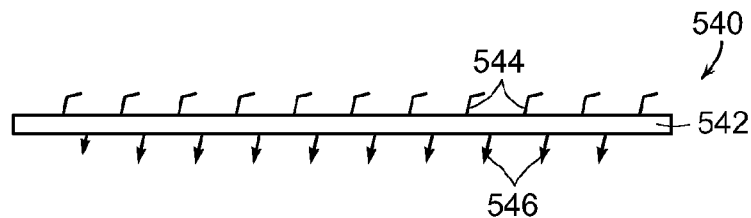
FIG. 11 is a side view of a tissue anchoring mesh in accordance with preferred embodiments of the invention.

Shown in FIG. 11 is a side view of an adhesion matrix or mesh 540 used in preferred embodiments of the invention. It can frequently be useful to employ such a mesh to facilitate wound adhesion and healing using an absorbable material that can adhere on both sides to tissues within a wound. Frequently, these tissue are of different types on opposite sides of the mesh. Thus, the mesh can include a conformable layer 542 having tissue anchors 544, 546 on both sides. However, as one side may be used to attach to the fatty or adipose tissue on the underside of a flap of skin, the first plurality of tissue anchors 544 has a shape and rigidity suitable for attaching to adipose tissue. The second plurality of tissue anchors can be shaped and sized to attach to less compliant tissues such as fascia or muscle. More rigid hooks or barbs are needed to enable this attachment.

Figure 12:
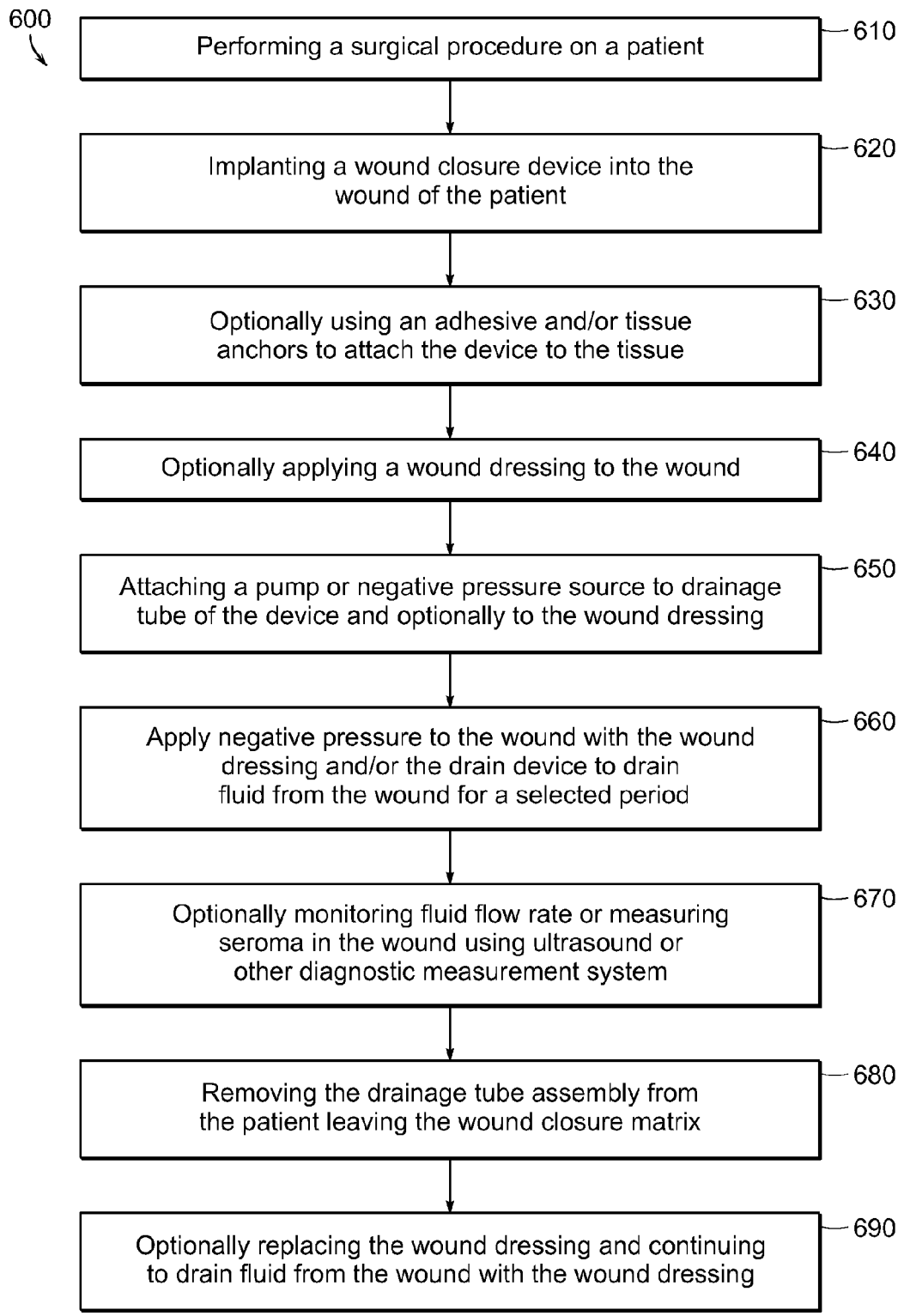
FIG. 12 is a process flow diagram illustrating a method of using a wound dressing and drainage system in accordance with preferred embodiments of the invention.

Shown in FIG. 12 is a sequence of steps in a method 600 of applying a drainage and wound dressing system in accordance with the invention. After performing a procedure 610 on a patient, a wound closure device is inserted 620 into the wound of a patient. This can be a combination of elements, such as meshes as shown in FIG. 11 in certain regions of the wound, and a drainage and mesh system as described generally herein in regions of the wound requiring drainage of fluid. This can also include the user 630 of adhesives and/or tissue anchors to enable more direct contact of tissues through the mesh and thereby improve the rate of healing. A wound dressing can also be applied 640 to the wound as described herein. A pump can then be attached 650 to the drainage system and/or the wound dressing and a negative pressure can be applied 660 to one or both elements to drain fluid and promote contact between tissues through the implanted mesh or matrix. The flow rate of fluid through each tube can be measured and recorded and the presence of fluid can be monitored 670 by ultrasound or other systems. The drainage tubing can be removed 680 when the drainage rate diminishes. The wound dressing can be replaced 690 as needed and can continue to be used to drain 690 the wound.

While this invention has been particularly shown and described with references to preferred embodiments thereof, it will be understood by those skilled in the art that various changes in form and/or details therein and equivalents thereof may be made without departing from the spirit and scope of the invention as set forth by the appended claims.

What is claimed is:

1. A method for treating a wound, the method comprising the steps of:
   positioning a matrix into a surgical wound, the matrix being connected to tissue in the wound with a plurality of tissue anchors extending from a surface of the matrix, wherein the matrix comprises a layer of biodegradable material having a plurality of spaced apart apertures such that tissue on a first side of the matrix contacts tissue on second side of the matrix through the spaced apart apertures in the matrix;
   attaching a negative pressure source to a drain device that is in fluid communication with the matrix, the drain device including a plurality of drain tubes extending across tube receiving regions of the matrix the plurality of drain tubes being positioned in the tube receiving regions between spaced apart apertures in the matrix;
   draining fluid from the wound for a period of time; and
   removing the plurality of drain tubes of the drain device from the wound such that the matrix remains in the wound.

2. The method of claim 1 further comprising attaching fascia tissue to the matrix with a first plurality of tissue anchors.

3. The method of claim 1 further comprising using an adhesive to attach tissue.

4. The method of claim 1 further comprising applying sufficient pressure to provide tissue contact through apertures of the matrix wherein the tissue on a first side of the matrix contacts tissue on a second side of the matrix through the apertures such that the tissue on the first side adheres to the tissue on the second side after at least partial healing.

5. The method of claim 4 wherein the apertures comprise at least 50 percent of a total matrix surface area.

6. The method of claim 1 further comprising applying a wound dressing to the wound.

7. The method of claim 6 further comprising applying a negative pressure to the wound dressing.

8. The method of claim 1 further comprising attaching the matrix with a second plurality of tissue anchors to adipose tissue.

9. The method of claim 1 further comprising attaching the matrix with a second plurality of tissue anchors to fascia and/or muscle tissue.

10. The method of claim 1 further comprising measuring a fluid flow rate through the drain device wherein the drain tubes are removed in response to a measure flow rate.

11. The method of claim 1 further comprising measuring an amount of seroma within the wound with an ultrasound device.

12. The method of claim 1 wherein the tube receiving regions are on a surface of the matrix and include channels that receive one or more drain tubes in the channels.

13. The method of claim 1 wherein the matrix comprises additional apertures that enable flow of fluid laterally into the plurality of drain tubes.

14. The method of claim 1 further comprising measuring a condition of the matrix within the wound with a diagnostic measurement device.

15. The method of claim 14 further comprising generating patient data with the diagnostic measurement device.

16. The method of claim 1 further comprising positioning the matrix wherein the matrix comprises a porous material between the apertures and the apertures comprise at least about 50 percent of the surface of the matrix.

17. The method of claim 1 further comprising at least partially closing the surgical wound such that the matrix is retained in the wound.

18. The method of claim 17 wherein the partially closed surgical wound comprises an opening for a drain tube.

19. The method of claim 1 wherein the positioning step further comprises positioning the matrix wherein the matrix includes a layer of a porous material that extends between the apertures.

20. The method of claim 19 wherein the plurality of apertures comprise at least about 50 percent of the surface area of the matrix.

21. The method of claim 1 further comprising folding a flap of tissue onto a side of the matrix.

22. The method of claim 1 wherein the plurality of apertures are open and comprise an area in a range of 75 to 80 percent of the surface area of the matrix.

* * * * *